US009492381B1

(12) United States Patent
Smith

(10) Patent No.: US 9,492,381 B1
(45) Date of Patent: *Nov. 15, 2016

(54) METHOD OF ADMINISTERING HYALURONAN FORMULATION FOR PREVENTING AND AMELIORATING OSTEOARTHRITIS

(71) Applicant: Reyn Pharma, LLC, Lexington, KY (US)

(72) Inventor: James D. Smith, Lexington, KY (US)

(73) Assignee: Reyn Pharma, LLC, Lexington, KY (US)

( * ) Notice: Subject to any disclaimer, the term of this patent is extended or adjusted under 35 U.S.C. 154(b) by 60 days.

This patent is subject to a terminal disclaimer.

(21) Appl. No.: 14/054,928

(22) Filed: Oct. 16, 2013

Related U.S. Application Data

(63) Continuation-in-part of application No. 12/572,641, filed on Oct. 2, 2009, now Pat. No. 8,598,144, which is a continuation-in-part of application No. 11/596,657, filed on Nov. 10, 2006, now abandoned, and a continuation-in-part of application No. 12/165,278, filed on Jun. 30, 2008, now abandoned.

(60) Provisional application No. 60/735,551, filed on Nov. 10, 2005, provisional application No. 60/937,909, filed on Jun. 30, 2007.

(51) Int. Cl.
   *A61K 31/728* (2006.01)
   *A61K 9/00* (2006.01)

(52) U.S. Cl.
   CPC ........... *A61K 9/0063* (2013.01); *A61K 31/728* (2013.01)

(58) Field of Classification Search
   None
   See application file for complete search history.

(56) References Cited

U.S. PATENT DOCUMENTS

| | | | |
|---|---|---|---|
| 4,623,539 A | 11/1986 | Tunc | |
| 4,647,453 A | 3/1987 | Meisner | |
| 4,808,576 A | 2/1989 | Schultz et al. | |
| 5,095,037 A | 3/1992 | Iwamitsu et al. | |
| 5,843,919 A | 12/1998 | Burger | |
| 5,985,850 A | 11/1999 | Falk et al. | |
| 6,013,641 A | 1/2000 | Lussow et al. | |
| 6,162,787 A | 12/2000 | Sorgente et al. | |
| 6,255,295 B1 | 7/2001 | Henderson et al. | |
| 6,333,304 B1 | 12/2001 | Bath et al. | |
| 6,346,519 B1 | 2/2002 | Petrus | |
| 6,387,382 B1* | 5/2002 | Saleh et al. | 424/401 |
| 6,391,861 B1 | 5/2002 | Cantor | |
| 6,391,864 B1 | 5/2002 | Stone | |
| 6,432,929 B1 | 8/2002 | Stone | |
| 6,451,771 B1 | 9/2002 | Henderson et al. | |
| 6,476,005 B1 | 11/2002 | Petito et al. | |
| 6,537,978 B1 | 3/2003 | Turley | |
| 6,607,745 B2 | 8/2003 | Leneau | |
| 6,608,041 B2 | 8/2003 | Hammerly | |
| 6,620,927 B2* | 9/2003 | Bulpitt et al. | 536/123.1 |
| 6,645,945 B1 | 11/2003 | Radomsky et al. | |
| 6,706,267 B1 | 3/2004 | Adalsteinsson et al. | |
| 6,924,273 B2 | 8/2005 | Pierce | |
| 6,979,679 B2* | 12/2005 | Marcum | 514/53 |
| 7,811,612 B2 | 10/2010 | Kim et al. | |
| 8,163,716 B1* | 4/2012 | Smith | 514/54 |
| 8,178,511 B1* | 5/2012 | Smith | 514/54 |
| 8,598,144 B1* | 12/2013 | Smith | 514/62 |
| 9,056,121 B1* | 6/2015 | Smith | |

OTHER PUBLICATIONS

Derwent Accession No. 2004-248590, Aug 20, 2003.*
Soltes et al., Biomed. Chromatog., 2002, 16, pp. 459-462.*
Equimed Europe LTD document; Mar. 9, 2010—found at the website: http://www.dugganvet.ie/productsvet/wp-content/uploads/2015/08/flyer_A4_SynVet50_030910-copy.pdf.*
James D. Smith, "Method of Administering Hyaluronan Formulation for the Amelioration of Osteoarthritis", U.S. Appl. No. 12/165,278, filed Jun. 30, 2008.
James D. Smith, "Method of Administering Hyaluronan Formulation for the Amelioration of Osteophytes", U.S. Appl. No. 12/485,265, filed Jun. 16, 2009.
James D. Smith, "Method of Administering Hyaluronan Formulation for the Amelioration of Osteopenia", U.S. Appl. No. 12/485,596, filed Jun. 16, 2009.
James D. Smith, "Hyaluronan Formulation", U.S. Appl. No. 11/595,657, filed Nov. 11, 2006.
Office Action mailed Sep. 14, 2008 in U.S. Appl. No. 11/595,657.
Response to Office Action mailed Sep. 14, 2008 and electronically submitted on Mar. 13, 2009.
Office Action mailed Jul. 23, 2009 in U.S. Appl. No. 11/595,657.
Mary K. Cowman, "$^1$H NMR of Glycosaminoglycans and Hyaluronic Acid Oligosaccharirdes in Aqueous Solution: The Amide Proton Environment", Archives of Biochemistry and Biophysics, vol. 230, No. 1, pp. 203-212, Apr. 1984.
Mary K. Cowman, "$^1$H NMR of Glycosaminoglycans and Hyaluronic Acid Oligosaccharirdes in Aqueous Solution: The Amide Proton Environment", Archives of Biochemistry and Biophysics, vol. 230, No. 1, pp. 203-212, Apr. 1984, (Abstract only).
M.F. McCarty, et al., "Sulfated Glycosaminoglycans and Glucosamine May Synergize in Promoting Synovial Hyaluronic Acid Synthesis", Medical Hypothesis (2000) 54(5), 798-802, Mar. 17, 1999.
M. Anthony Pogrel, et al., "Hyaluronan (hyaluronic acid) in Human Saliva", Archives of Oral Biology, vol. 41, No. 7, pp. 667-671, (1996).

(Continued)

*Primary Examiner* — Traviss C McIntosh, III
(74) *Attorney, Agent, or Firm* — Curatolo Sidoti Co., LPA; Salvatore A. Sidoti; Joseph G. Curatolo

(57) ABSTRACT

Disclosed is a method for mitigating or ameliorating osteoarthritis in vertebrate subjects including administering to a subject a therapeutically effective amount of an exogenous hyaluronan formulation. Also disclosed is an oral or parenteral hyaluronan composition comprising a polydisperse hyaluronan and a pharmaceutically acceptable carrier, and a method of manufacturing the composition.

30 Claims, 5 Drawing Sheets

(56) References Cited

OTHER PUBLICATIONS

A Rossler, et al., "Plasma Hyaluronan Concentration: No Circadian Rhythm but Large Effect of Food Intake in Humans", Eur J Appl Physiol, vol. 78, No. 6, pp. 573-577, (1998).
Hideki Sato, et al., Antioxidant Activity of Synovial Fluid, Hyaluronic Acid, and Two Subcomponents of Hyaluronic Acid, Arthritis and Rheumatism, vol. 31, No. 1 (Jan. 1998).
Chris Tuckwell, "Velvet Antler, a Summary of the Literature on Health Benefits", Australian Government—Rural Industries Research and Development Corporation, Nov. 2003.
M.Anthony Pogrel, et al., "Hyaluronan (hyaluronic acid) and Its Regulation in Human Saliva by Hyaluronidase and its Inhibitors", Journal of Oral Science, vol. 45, No. 2, 2003, pp. 85-91, Publication Date: May 19, 2003.
Derwent Acc No. 2004-248590: Aug. 20, 2003 CN 1436537 to Zhang.
USPTO Office Action mailed Oct. 3, 2011 for U.S. Appl. No. 12/485,265, filed Jun. 16, 2009.
USPTO Office Action mailed Jul. 7, 2011 for U.S. Appl. No. 12/485,596, filed on Jun. 16, 2009.
Kim, Chang Hwan, et al. Therapeutic Effect onf Hyaluronic Acid on Experimental Osteoarthritis of Ovine Tetra Mandibular Joint, J. Vet. Med. Sci. (2001) vol. 163, No. 10, pp. 1083-1089.
"Bone Spurs", downloaded from Mayoclinic.com, revised Jan. 5, 2010, pp. 1-16.
Stancikova, et al. The Effects of Hyaluronan on Bone Resportion and Bone Mineral Density in a Rat Model of Estrogen Deficiency-Induced Osteopenia, Int. J. Tissue React, 2004 26 (½), pp. 9-16.

\* cited by examiner

METHOD OF ADMINISTERING HYALURONAN FORMULATION FOR PREVENTING AND AMELIORATING OSTEOARTHRITIS

CROSS REFERENCE TO RELATED APPLICATIONS

This application is a continuation-in-part of U.S. Ser. No. 12/572,641 filed Oct. 2, 2009, which is a continuation-in-part of U.S. application Ser. No. 11/595,657, filed Nov. 10, 2006, which claims the benefit of the filing date under 35 U.S.C. §119(e) of U.S. Provisional Application for Patent Ser. No. 60/735,551 filed on Nov. 10, 2005, U.S. Ser. No. 12/572,641 is also a continuation-in-part of U.S. application for patent Ser. No. 12/165,278, filed Jun. 30, 2008, which claims the benefit of the filing date under 35 U.S.C. §119(e) of U.S. Provisional Application for Patent Ser. No. 60/937,909 filed on Jun. 30, 2007, all of which are hereby incorporated by reference.

TECHNICAL FIELD

The present disclosure relates to a method of administering a composition comprising a therapeutically effective amount of an exogenous hyaluronan formulation to a subject for preventing, slowing, attenuating, mitigating, and/or ameliorating the loss of articular cartilage in osteoarthritis.

BACKGROUND

Osteoarthritis is characterized by the progressive loss of articular cartilage. Eventually, in many cases, the entirety of the articular cartilage in certain diarthrodial joints such as the knee, where the femur and tibia articulate, is lost.

Joint injury and osteoarthritis are major causes of lameness and disability. Mammals have pain that typically worsens with weight-bearing and activity and improves with rest. Inflammation may be mild and localized in the affected joint. Although the etiology of osteoarthritis remains unknown, biomechanical stresses and biochemical changes in the articular cartilage, subchondral bone and synovial membrane, as well as genetic factors, are all important in its pathogenesis. The synovial fluid's capacity to lubricate and to absorb impact is reduced in affected joints. These changes are due to a reduction in the size, concentration and quality of hyaluronan molecules naturally present in synovial fluid.

Commonly used treatments and medications only provide palliative care. Palliative care is defined as any form of medical care or treatment that concentrates on reducing the severity of disease symptoms, rather than halting or delaying progression of the disease or providing a cure. Non-Steroidal Anti-inflammatory Drugs (NSAIDs) are frequently prescribed or self-administered ad libitum. Types include aspirin, ibuprofen, acetaminophen, and naproxen. Although NSAIDs work well for their intended purpose, long-term use of these drugs can cause stomach problems such as ulcers and bleeding.

In April 2005, the FDA asked manufacturers of NSAIDs to include a warning label on their product to alert users of an increased risk for cardiovascular events (heart attacks and strokes) and gastrointestinal bleeding. Certain NSAIDs may also weaken bone and increase the risk of bone fractures.

COX-2 inhibitors (coxibs) are also used to treat symptoms. Coxibs block an inflammation-promoting enzyme called COX-2. This class of drugs was initially believed to work as well as traditional NSAIDs, but with fewer stomach problems. However, numerous reports of heart attacks and strokes have prompted the FDA to re-evaluate the risks and benefits of the COX-2s. Certain COX-2s have been withdrawn from the US market following reports of heart attacks in some patients taking the drugs. COX-2s still commercially available are labeled with strong warnings and a recommendation that it be prescribed at the lowest possible dose for the shortest duration possible. However, neither NSAIDs nor COX-2 inhibitors are known to stop or restore the loss of articular cartilage, which is the hallmark of osteoarthritis and the cause of the symptoms.

Steroids and artificial joint fluid (Synvisc, Hyalgan, etc.) can be injected directly into the joint capsule to reduce pain and inflammation for up to six months but have attendant injection site risks and do not improve the underlying cartilage condition.

Natural substances marketed in the United States as dietary supplements are also administered in cases of osteoarthritis. In particular, glucosamine, chondroitin sulfate, and methylsulfonylmethane (MSM) are administered in order to provide some relief from the symptoms of osteoarthritis. However, none of these substances is known to address cartilage loss, the root cause of osteoarthritis symptoms.

While exogenous hyaluronan has been administered via intraarticular and intravenous injections to mammals, it is not generally known that hyaluronan in an effective amount could be absorbed following perioral administration. Furthermore, there is no teaching in the art of a method for preventing, slowing, attenuating, mitigating, and/or ameliorating the loss of articular cartilage in osteoarthritis in a vertebrate subject, the method comprising the step of administering a composition comprising a therapeutically effective amount of an exogenous hyaluronan to the subject. The present disclosure provides such a method.

SUMMARY

Disclosed is a method for preventing, slowing, attenuating, mitigating, and/or ameliorating the loss of articular cartilage in osteoarthritis in a vertebrate subject, the method comprising administering a composition comprising a therapeutically effective amount of an exogenous hyaluronan formulation to a vertebrate subject.

Also disclosed is a composition comprising a polydisperse hyaluronan formulation and a pharmaceutically acceptable carrier.

DETAILED DESCRIPTION

Figure 1:
FIG. 1 is a photograph of the histopathology tissue section of a Control Mouse knee (Group A untreated Control Mouse six week post surgery; average score 5.33/24).
Figure 2:
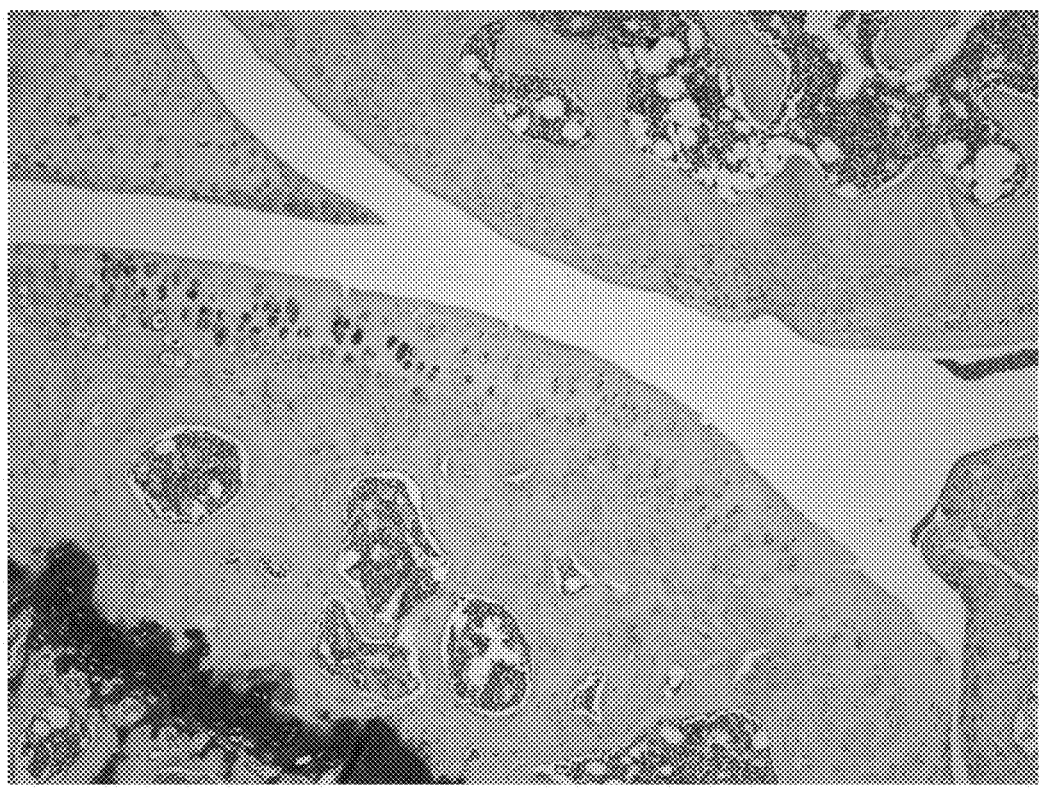
FIG. 2 is a photograph of the histopathology tissue section of a Control Mouse knee (Group B Saline 3 week Control average score 10.7/24).
Figure 3:
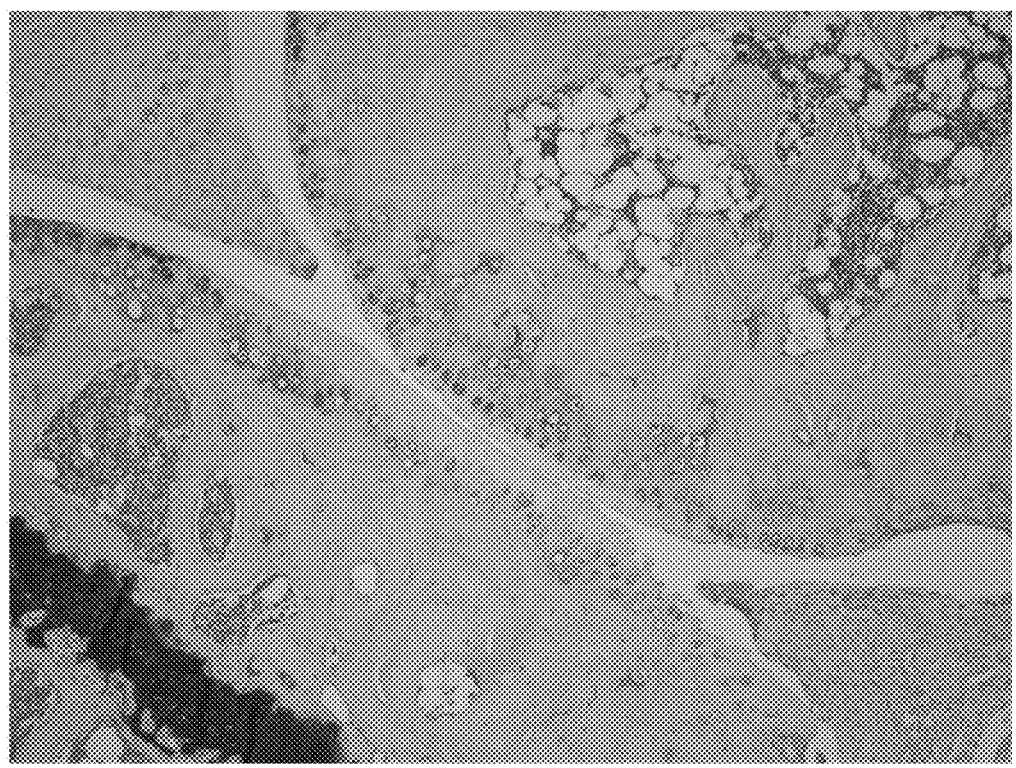
FIG. 3 is a photograph of the histopathology tissue section of a Control Mouse knee (Group C Saline 6 week Control average score 12.8/24).
Figure 4:
FIG. 4 is a photograph of the histopathology tissue section of a Treatment Mouse knee (Group D MBH3™ 3 week Treated average score 7.2/24).
Figure 5:
FIG. 5 is a photograph of the histopathology tissue section of a Treatment Mouse knee (Group E MBH3™ 6 week Treated average score 7.8/24).

Disclosed is a method of administering a modified hyaluronan biopolymer formulation to a vertebrate subject for the purposes of preventing, slowing, attenuating, mitigating, and/or ameliorating the loss of loss of articular cartilage in osteoarthritis. By mitigating or ameliorating the loss of articular cartilage in the subject, the method also treats joint discomfort that is associated with osteoarthritis. The method comprises administering a composition comprising a therapeutically effective amount of exogenous hyaluronan biopolymer to the subject.

The method of administering a therapeutically effective amount of the hyaluronan biopolymer to a subject may be accomplished by oral or parenteral administration. With respect to oral administration, the hyaluronan formulation may be administered directly into the subject's mouth. Alternatively, oral administration may be achieved by including the therapeutically effective amount of the hyaluronan formulation in the subject's food or beverage such as water. For example, the hyaluronan formulation may be provided in the form of a syrup that is useful for adding to food rations. According to certain illustrative embodiments, parenteral administration of the therapeutically effective amount of the hyaluronan may comprise subcutaneous administration, intramuscular administration, and intravenous administration. According to illustrative embodiments, the method of administering a therapeutically effective amount of the hyaluronan biopolymer to a subject may be accomplished by intra-articular administration injection of a subject.

A therapeutically effective amount of hyaluronan biopolymer per kg body weight of the test subject can be determined by one having ordinary skill in the art without having to resort to undue experimentation. According to certain illustrative embodiments, and without limitation, therapeutically effective amounts may comprise from about 0.2 to about 5 mg per kg body weight of the subject, from about 0.4 to about 4 mg per kg body weight of the subject, from about 0.6 to about 3 mg per kg body weight of the subject, from about 0.8 to about 2 mg per kg body weight of the subject, and about 1 mg per kg body weight of the subject.

The term "hyaluronan" as used herein refers to hyaluronic acid or any physiological salt form of hyaluronic acid. The hyaluronan biopolymer is polydisperse and therefore comprises a blend or mixture of hyaluronan polymers having different molecular masses. Without limitation, hyaluronan biopolymers that are administered to the vertebrate subject may comprise a blend of polymers having molecular weights in range from about 50,000 to about 8,000,000 Daltons. By way of illustration, suitable hyaluronan polymers may comprise molecular weights from about 500,000 to about 3,000,000 Daltons, from about 500,000 to about 2,500,000 Daltons, from about 750,000 to about 2,250,000 Daltons, from about 1,000,000 to about 2,000,000 Daltons, from about 1,250,000 to about 1,750,000 Daltons, or from about 1,375,000 to about 1,625,000 Daltons. According to certain embodiments, the biopolymers comprise an average molecular weight of about 1,500,000 Daltons.

The hyaluronan formulation thus comprises hyaluronan molecules of appropriate size(s). For optimal absorption by a warm-blooded mammal, the hyaluronan molecule must be shortened in length. Long chains of hyaluronan molecules tend to break down in an acidic environment, because the acid cleaves at and breaks some of the glycosidic bonds within the hyaluronan molecule. Accordingly, degradation of long-chain hyaluronan polymers by acid can yield readily absorbed hyaluronan polymers. It has been found that organic acids, without limitation, citric acid or ascorbic acid are useful and effective in lowering the pH and in cleaving longer-chain hyaluronan polymers into somewhat shorter hyaluronan polymers which are more readily absorbed along a mammal's gastrointestinal tract.

According to illustrative embodiments, the biopolymer composition comprises a product of microbial fermentation. By producing the polymer by extra-cellular microbial fermentation, it is considered to be a vegan product. Accordingly, the hyaluronan may contain no animal derived materials, which minimizes the risk of transmission of animal spongiform encephalopathy. Producing the hyaluronan polymer by microbial fermentation also results in more consistent molecular profile, molecular weight and narrow polydispersity that is optimized for oral bioavailability. According to certain embodiments, the formulation may be made, for example, from sodium hyaluronate that is bacterially synthesized.

The hyaluronan composition comprises a pharmaceutically acceptable carrier that is safe for human or veterinary consumption. Without limitation, and by way of example only, a suitable carrier for the hyaluronan composition is water.

According to certain embodiments, the hyaluronan formulation may contain at least one non-water excipient that is pharmaceutically acceptable. Without limitation, and by way of example only, a suitable excipient for the hyaluronan composition comprises sodium chloride. Any of many excipients described in the current edition of the Handbook of Pharmaceutical Excipients (5th edition, R C Rowe et al, eds.) may be suitable for inclusion in a formulation according to the invention. A non-limiting example of such an excipient is xanthan gum.

The hyaluronan composition may also include a pH altering agent. The pH altering agent included hyaluronan composition may comprise an inorganic or organic acid. Without limitation, and by way of example only, a suitable pH altering agent for the hyaluronan composition comprises a pharmaceutically acceptable organic acid, such as citric acid or ascorbic acid. According to certain embodiments, and without limitation, citric acid or ascorbic acid may be included in the hyaluronan composition in an amount effective to provide a pH of the hyaluronan composition that is between about 2.5 and about 7.

According to certain illustrative embodiments, the pH altering agent may be included in the hyaluronan composition in an amount effective to provide a pH of the hyaluronan composition that is between about 2.5 and about 5.5.

According to further illustrative embodiments, the pH altering agent may be included in the hyaluronan composition in an amount effective to provide a pH of the hyaluronan composition that is between about 2.5 and about 4.5.

According to further illustrative embodiments, the pH altering agent may be included in the hyaluronan composition in an amount effective to provide a pH of the hyaluronan composition that is between about 4.5 and about 5.5.

Without limitation, and by way of example only, a suitable pH altering agent for the hyaluronan composition comprises citric acid. According to certain embodiments, and without limitation, citric acid is the pH altering agent and it is included in the hyaluronan composition in an amount effective to provide a pH of the hyaluronan composition that is between about 2.5 and about 7.

According to certain illustrative embodiments, the pH altering agent is citric acid and is included in the hyaluronan composition in an amount effective to provide a pH of the hyaluronan composition that is between about 2.5 and about 5.5.

According to certain illustrative embodiments, the pH altering agent is citric acid and is included in the hyaluronan composition in an amount effective to provide a pH of the hyaluronan composition that is between about 2.5 and about 4.5.

According to certain illustrative embodiments, the pH altering agent is citric acid and is included in the hyaluronan composition in an amount effective to provide a pH of the hyaluronan composition that is between about 4.5 and about 5.5.

Without limitation, and by way of example only, a suitable pH altering agent for the hyaluronan composition comprises ascorbic acid. According to certain embodiments, and without limitation, citric acid is the pH altering agent and it is included in the hyaluronan composition in an amount effective to provide a pH of the hyaluronan composition that is between about 2.5 and about 7.

According to certain illustrative embodiments, the pH altering agent is ascorbic acid and is included in the hyaluronan composition in an amount effective to provide a pH of the hyaluronan composition that is between about 2.5 and about 5.5.

According to certain illustrative embodiments, the pH altering agent is ascorbic acid and is included in the hyaluronan composition in an amount effective to provide a pH of the hyaluronan composition that is between about 2.5 and about 4.5.

According to certain illustrative embodiments, the pH altering agent is ascorbic acid and is included in the hyaluronan composition in an amount effective to provide a pH of the hyaluronan composition that is between about 4.5 and about 5.5.

During the manufacture of the hyaluronan formulation, the inclusion of the pH altering agent provides a hyaluronan formulation lowers the pH and maintains the pH in the range of about 2.5 to about 7 for a desired period of time. According to certain illustrative embodiments, during the manufacture of the hyaluronan formulation, the inclusion of the pH altering agent provides a hyaluronan formulation lowers the pH and maintains the pH in the range of about 2.5 to about 4.5 for a desired period of time. The limited period of time may be less than about sixteen hours. The limited period of time may be less than about eight hours. The limited period of time may be less than about four hours. The limited period of time may be less than about two hours. The limited period of time may be less than about one hour. A person skilled in the art will recognize various means of thus lowering the pH. The intrinsic viscosity and the specific gravity of the formulation are also important parameters for manufacturing optimization.

According to certain illustrative embodiments, the composition comprises a therapeutically effective amount of hyaluronan and an antimicrobial preservative or stabilizer. Any known antimicrobial preservative that is generally regarded as safe for human or veterinary consumption may be included in the hyaluronan composition. Without limitation, according to certain embodiments, suitable antimicrobial preservatives include potassium sorbate, sodium benzoate and mixtures thereof. The antimicrobial preservative(s) may be present in an amount of from about 0.1 mg/mL to about 5 mg/mL. Inclusion of such a preservative imparts a shelf-life to a formulation of as much as six months.

The biopolymer composition and method of administration may be useful for treating afflictions of cartilage of a wide variety of vertebrate species. For example, and by way of example only, the hyaluronan composition may be administered to any of rat, murine, human, equine, canine or feline species.

The hyaluronan composition and method of administration to the vertebrate subject is useful in treating osteoarthritis. The composition or method is useful in treating the osteoarthritis condition that is a result of either an injury or a degenerative process other than injury.

The hyaluronan may be formulated into a wide variety of orally ingestible compositions. Hyaluronan is a non-sulfated glycosaminoglycan which can be dispensed in aqueous oral formulations. The hyaluronan may be formulated with an acceptable carrier to provide an orally ingestible liquid or a solid or semi-solid food product. Liquid forms include solutions, suspensions, emulsions, gels, syrups, and the like. According to certain illustrative embodiments, the hyaluronan composition may be formulated with an orally ingestible liquid carrier to provide an orally ingestible hyaluronan composition. For example, the hyaluronan may be formulated with an orally ingestible liquid carrier to provide a beverage, dietary supplement formulation, or nutritional supplemental. The beverages, dietary supplements and nutritional supplements may be provided ready for oral ingestion or may be provided in a concentrate for that requires dilution with acceptable liquids prior to oral ingestion. According to alternative embodiments, the hyaluronan may be formulated into other orally ingestible product forms, such as powders, pills, lozenges, tablets, caplets, capsules, gel capsules, dissolvable films and the like. Flavoring agents may also be added to the hyaluronan compositions to provide a more palatable orally ingestible composition.

The orally administrable hyaluronan composition may further include nutritionally effective amounts of an additional supplement. According to certain embodiments, the hyaluronan composition further comprises nutritionally effective amounts of at least one vitamin, or at least one mineral or a combination of at least one vitamin and at least one mineral. According to certain embodiments, the hyaluronan composition comprises a therapeutically effective amount of hyaluronan and a nutritionally effective amount of at least one vitamin. According to certain embodiments, the hyaluronan composition comprises a therapeutically effective amount of hyaluronan and a nutritionally effective amount of more than one different vitamin. According to certain embodiments, the hyaluronan composition comprises a therapeutically effective amount of hyaluronan and a nutritionally effective amount of at least one mineral. According to certain embodiments, the hyaluronan composition comprises a therapeutically effective amount of hyaluronan and a nutritionally effective amount of more than one different mineral. According to certain embodiments, the hyaluronan composition comprises a therapeutically effective amount of hyaluronan and a nutritionally effective amount of at least one vitamin and at least one mineral. According to certain embodiments, the hyaluronan composition comprises a therapeutically effective amount of hyaluronan and a nutritionally effective amount of more than one different vitamin and at least one mineral. According to certain embodiments, the hyaluronan composition comprises a therapeutically effective amount of hyaluronan and a nutritionally effective amount of at least one vitamin and more than one different mineral. According to certain embodiments, the hyaluronan composition comprises a therapeutically effective amount of hyaluronan and a nutritionally effective amount of more than one different vitamin and more than one different mineral.

The pharmacokinetics of the hyaluronan formulation are noteworthy. Scintigraphy of a dog to which has been administered a single oral administration of a technetium 99m- labeled formulation demonstrates absorption and distribution to organs, joints and bones within two hours post-administration. Scintigraphy of a rat to which has been administered a single oral administration of a technetium 99m-labeled formulation demonstrates absorption and distribution to organs, joints and bones within four hours post-administration. Accordingly, the present hyaluronan formulation is effectively delivered to joints after a single oral administration. Traces of a formulation according to the invention were observed in as little as 30 minutes post-administration following a single oral administration.

The present hyaluronan formulation by preventing, slowing, attenuating, mitigating, and/or ameliorating the loss of articular cartilage confers chondroprotection to a mammal to which the formulation is administered if the mammal is in need of chondroprotection. A formulation according to the invention confers disease modification to a mammal to which the formulation is administered if the mammal is in need of disease modification. By providing disease modification, the administration of the formulation enhances chondrocyte hyaluronan and proteoglycan syntheses, thereby reducing the production and activity of proinflammatory mediators and matrix metalloproteinases. This is significant for reducing nerve impulses and nerve sensitivity associated with the pain of osteoarthritis. Preventing, slowing, attenuating, mitigating, and/or ameliorating the loss of articular cartilage also results in a lessening of inflammation, and a reduction in pain, in a mammal to which the formulation is administered.

The formulation also imparts salutary regulatory effects on granulocytes, monocytes, fibroblasts, and endothelial cells, as well as on the healing of wounds and various joint disorders. Animal-based studies have demonstrated positive effects of the formulation on pain in the joint and on heat shock proteins, which are significant in osteoarthritis. In addition to the stimulating effect on hyaluronan-producing synoviocytes, the anti-inflammatory and analgesic properties according to the invention provide symptomatic relief from the pain associated with osteoarthritis. The formulation protects human cartilage in explant culture and was shown to facilitate restoration of proteoglycan in damaged cartilage.

The hyaluronan composition may also include a drug component alone or in addition to the nutritional supplemental.

Additionally provided is a method for manufacturing a hyaluronan formulation, said formulation being useful for the purposes of preventing, slowing, attenuating, mitigating, and/or ameliorating the loss of loss of articular cartilage in osteoarthritis. The method comprises the step of maintaining the pH of an aqueous solution containing hyaluronan to a pH of from about 2.5 to about 7 for a desired period of time. According to certain embodiments, the method comprises the step of maintaining the pH of an aqueous solution containing hyaluronan to a pH of from about 2.5 to about 4.5.

EXAMPLES

The following examples are provided to further illustrate the hyaluronan composition and method of administering the exogenous hyaluronan to vertebrate subjects. It should be noted that the examples are provided for illustration and should not be construed to limit the scope of the composition or method of administering the composition in any manner.

Effects of MBH3™ (Hyaluronan Biopolymer) on Cartilage Loss in a Mouse Model of Monoarthritis Osteoarthritis (OA) is characterized by progressive articular cartilage loss. A study was designed and conducted using an established histopathological scoring system to evaluate specifically the effects of an orally administered, polydisperse hyaluronan biopolymer (MBH3™, Cogent Solutions Group LLC) in a mouse model of monoarthritis.

Thirty 10 week old male C57BL/6 mice purchased from Charles River Laboratories were subjected to a meniscotibial ligament transaction surgery of the left knee. This surgery creates a slowly advancing instability condition that mimics the loss of articular cartilage in humans with OA. After six weeks mice were randomly assigned to 5 groups. Group A (Untreated Controls N=6) was euthanized, their knees decalcified, paraffin embedded, stained with Saffrin-O and scored (Pritzker et al.) to confirm disease onset and cartilage loss. A histopathological score of 1 indicates articular cartilage which is intact and pristine. A score of less than 10 indicates that a great deal of healthy articular cartilage remains. A histopathological score of 24 indicates total loss of articular cartilage as is observed in very severe cases. Following confirmation of cartilage loss at week 6 post surgery Group B (Controls, N=6) was gavaged 5 days/week for 3 weeks with saline; Group C (Controls, N6) was gavaged 5 days/week for 6 weeks with saline; Group D (Treated, N=6) was gavaged 5 days/week for 3 weeks with MBH3™ at a dose of 10 mg/kg; and Group E (Treated, N=6) was gavaged 5 days/week for 6 weeks with MBH3™ at a dose of 10 mg/kg. At the end of three weeks of treatment Groups B and D were euthanized, scored and compared. At the end of the six weeks treatment Groups C and E were euthanized, scored, and compared.

The average score of Group A (6 week surgery) was 5.33/24, indicating the onset of osteoarthritis disease and serving as a baseline. The average score in Group B (3 week saline control) was 10.7/24 versus the average score of Group D (3 week MBH3™ treated) was 7.2/24: the average score in Group C (6 week saline control) was 12.8/24 versus the average score of Group E was 7.8/24. The result of this study strongly supports the disease modifying and protective benefits of MBH3™ when used in an established model of osteoarthritis. To our knowledge this is the first time that an orally administered, exogenous hyaluronan biopolymer has been shown to have such benefits.

Likewise, through parenteral administration of a buffered hyaluronan solution, such as through subcutaneous or intramuscular administration, similar effects are observed. It will be apparent to those skilled in the art to which the present invention pertains how to make and how to use such a buffered hyaluronan solution for parenteral administration.

While the method for administering hyaluronan to vertebrate subject has been described above in connection with certain illustrative embodiments, it is to be understood that other embodiments may be used or modifications and additions may be made to the described embodiments for performing the same function without deviating therefrom. Furthermore, all embodiments disclosed are not necessarily in the alternative, as various embodiments may be combined to provide the desired characteristics. Variations can be made by one having ordinary skill in the art without departing from the spirit and scope of the disclosed method. Therefore, the method should not be limited to any single embodiment, but rather construed in breadth and scope in accordance with the recitation of the attached claims. Equivalents will be readily apparent to those skilled in the art.

I claim:

1. A method for slowing, attenuating, mitigating, and/or ameliorating the loss of articular cartilage in a vertebrate subject, the method comprising orally administering a liquid composition comprising a therapeutically effective amount of exogenous hyaluronan composition comprising hyaluronan polymer and a pharmaceutically acceptable carrier to the subject, wherein the pH of the composition is about 2.5 to about 4.5.

2. The method of claim 1, wherein the hyaluronan comprises an average molecular weight from about 750,000 to about 2,250,000 Daltons.

3. The method of claim 2, wherein the hyaluronan comprises an average molecular weight from about 1,000,000 to about 2,000,000 Daltons.

4. The method of claim 3, wherein the hyaluronan comprises an average molecular weight from about 1,250,000 to about 1,750,000 Daltons.

5. The method of claim 4, wherein the hyaluronan comprises an average molecular weight from about 1,375,000 to about 1,625,000 Daltons.

6. The method of claim 5, wherein the hyaluronan comprises an average molecular weight about 1,500,000 Daltons.

7. A method for slowing, attenuating, mitigating, and/or ameliorating joint discomfort in a vertebrate subject in need thereof, the method comprising orally administering to the subject a liquid composition comprising a therapeutically effective amount of hyaluronan and a pharmaceutically acceptable carrier, wherein the pH of the composition is between about 2.5 and about 4.5.

8. The method of claim 7, wherein the hyaluronan comprises an average molecular weight from about 750,000 to about 2,250,000 Daltons.

9. The method of claim 8, wherein the hyaluronan comprises an average molecular weight from about 1,000,000 to about 2,000,000 Daltons.

10. The method of claim 9, wherein the hyaluronan comprises an average molecular weight from about 1,250,000 to about 1,750,000 Daltons.

11. The method of claim 10, wherein the hyaluronan comprises an average molecular weight from about 1,375,000 to about 1,625,000 Daltons.

12. The method of claim 11, wherein the hyaluronan comprises an average molecular weight about 1,500,000 Daltons.

13. A method for slowing, attenuating, mitigating, and/or ameliorating joint discomfort in a vertebrate subject in need thereof, the method comprising orally administering to the subject a liquid dietary supplement comprising a therapeutically effective amount of hyaluronan and a pharmaceutically acceptable carrier, wherein the pH of the composition is between about 2.5 and about 4.5.

14. The method of claim 13, wherein the hyaluronan comprises an average molecular weight from about 750,000 to about 2,250,000 Daltons.

15. The method of claim 14, wherein the hyaluronan comprises an average molecular weight from about 1,000,000 to about 2,000,000 Daltons.

16. The method of claim 15, wherein the hyaluronan comprises an average molecular weight from about 1,250,000 to about 1,750,000 Daltons.

17. The method of claim 16, wherein the hyaluronan comprises an average molecular weight from about 1,375,000 to about 1,625,000 Daltons.

18. The method of claim 17, wherein the hyaluronan comprises an average molecular weight about 1,500,000 Daltons.

19. A method for reducing joint pain in a vertebrate subject in need thereof, the method comprising orally administering to the subject a liquid dietary supplement comprising a therapeutically effective amount of hyaluronan and a pharmaceutically acceptable carrier, wherein the pH of the dietary supplement is between about 2.5 and about 4.5.

20. The method of claim 19, wherein the hyaluronan comprises an average molecular weight from about 750,000 to about 2,250,000 Daltons.

21. The method of claim 20, wherein the hyaluronan comprises an average molecular weight from about 1,000,000 to about 2,000,000 Daltons.

22. The method of claim 21, wherein the hyaluronan comprises an average molecular weight from about 1,250,000 to about 1,750,000 Daltons.

23. The method of claim 22, wherein the hyaluronan comprises an average molecular weight from about 1,375,000 to about 1,625,000 Daltons.

24. The method of claim 23, wherein the hyaluronan comprises an average molecular weight about 1,500,000 Daltons.

25. A method for supporting joint health in a vertebrate subject in need thereof, the method comprising orally administering to the subject a liquid composition comprising a therapeutically effective amount of hyaluronan and a pharmaceutically acceptable carrier, wherein the pH of the liquid composition is between about 2.5 and about 4.5.

26. The method of claim 25, wherein the hyaluronan comprises an average molecular weight from about 750,000 to about 2,250,000 Daltons.

27. The method of claim 26, wherein the hyaluronan comprises an average molecular weight from about 1,000,000 to about 2,000,000 Daltons.

28. The method of claim 27, wherein the hyaluronan comprises an average molecular weight from about 1,250,000 to about 1,750,000 Daltons.

29. The method of claim 28, wherein the hyaluronan comprises an average molecular weight from about 1,375,000 to about 1,625,000 Daltons.

30. The method of claim 29, wherein the hyaluronan comprises an average molecular weight about 1,500,000 Daltons.

* * * * *